(12) United States Patent
Leko

(10) Patent No.: US 7,172,774 B2
(45) Date of Patent: Feb. 6, 2007

(54) COMPOSITION FOR PROTECTION AND REGENERATION OF STRUCTURE AND FUNCTION OF THE LIVER

(76) Inventor: Vladimir Leko, Istarska 7, HR-34 000, Slavonska Pozega (HR)

( * ) Notice: Subject to any disclaimer, the term of this patent is extended or adjusted under 35 U.S.C. 154(b) by 0 days.

(21) Appl. No.: 10/880,749

(22) Filed: Jun. 28, 2004

(65) Prior Publication Data
US 2005/0003028 A1 Jan. 6, 2005

(51) Int. Cl.
*A61K 36/28* (2006.01)
*A61K 36/286* (2006.01)
*A61K 36/00* (2006.01)

(52) U.S. Cl. .................. 424/764; 424/747; 424/778; 424/773; 424/725

(58) Field of Classification Search ................ 424/725, 424/195.1, 764, 747, 778, 773
See application file for complete search history.

(56) References Cited

U.S. PATENT DOCUMENTS 6,262,019 B1 * 7/2001 Keller et al. .................... 514/2

FOREIGN PATENT DOCUMENTS

| RU | 2014842 C1 * | 6/1994 |
| RU | 2087154 C1 * | 8/1997 |
| WO | WO 03/035087 A1 * | 5/2003 |

* cited by examiner

*Primary Examiner*—Patricia Leith
(74) *Attorney, Agent, or Firm*—St. Onge Steward Johnston & Reens LLC

(57) ABSTRACT

The composition of herbal origin in which the active substance is sylimarin, characterized by the fact that, apart from the active substance which in the composition can be present in isolated form or like a component of St. Mary thistle plant, also contains the following components that are in synergic relation with the active substance: *Millefolii flos*—yarrow flower *Taraxaci radix*—dandelion root *Menthae piperitae* folium—peppermint leaf *Cardui mariae folium*—St. Mary thistle leaf *Helichrysi Menyanthes trifoliata folium*—buckbean leaf.

3 Claims, No Drawings

COMPOSITION FOR PROTECTION AND REGENERATION OF STRUCTURE AND FUNCTION OF THE LIVER

DESCRIPTION OF THE INVENTION

1. Field which the Invention Refers to

A 61 K 35/78 Materials from plants

31/33 Heterocyclic compounds

31/335 Heterocyclic compounds having oxygen as the only ring hetero atom

31/34 Heterocyclic compounds having five-membered rings with one oxygen as the only ring hetero atom 31/58 Compounds containing heterocyclic rings 31/665 Compounds having oxygen as a ring hetero atom 2. Technical Problem The most common causes of liver poisoning are:

alcohol—as "the greatest enemy to the liver"

medicaments—some remedies as paracetamol and some antibiotics toxins (xenobiotics) as falodin, a-amaritin (mushroom toxins)

viruses; for instance, hepatitis viruses, exotic viruses (ebola), Epstein Barr virus (mononucleosis), rubella viruses exposure to industrial chemicals When liver is exposed to some of these agents, or chemotherapy, radiation, drugs or to risks coming from the surrounding (pesticides, heavy metals, car exausts, passive smoking), the ability of its regeneration is decreasing or even ceasing.

Hepatitis has particularly proved itself as a very difficult and infectious disease. Since interferon-based remedies, having been used heretofore, have been succesfull only with 40% of the patients, death would often be the result of the illness.

The most often case is that, when infected by hepatitis, liver is not able to recover quickly enough, thus resulting in a fatty liver.

The goal of this application is a new type of liver remedy, addiotional to those that have been used heretofore. This remedy can be administered independently.

DESCRIPTION OF THE INVENTION IN DETAIL

Intensive efforts on St. Mary Thistle, or Blessed Milk Thistle, (Cardui mariae) preparations have been made during the last 30 years, and its appliance in traditional medicine is 2000 years old. There is almost no country and/or pharmaceutical company that does not produce at least one composition based on St. Mary thistle. In most cases, they are sylimarin-based compositions, isolated from plant seeds. The biggest disadvantages of this kind of compositions are:

weak solubility of sylimarin in water weak re-absorbtion into digestive system

Due to these two disadvantages, there are two requirements that have to be met if the composition is to be effective:

1. Certain minimal amount of sylimarin in St. Mary thistle seeds (3.5% according to German pharmacopeia, 4% according to US pharmacopeia)

2. Ready preparations must contain exactly determined amount of sylimarin

Although the existence of sylimarin in St. Mary thistle leaves has been proved, little effort has been made regarding its quantitative and qualitative determination. Thus, the use of St. Mary thistle leaf was given up because the concentration of sylimarin in St. Mary thistle fruit is higher, and sylimarin itself can easily be determined by using thin-layer chromatography, according to pharmacopeia. So, the "problem" with sylimarin from St. Mary thistle leaf is that it is linked into compounds. This was proved by the analyses of our herbal composition. The composition is made from St. Mary Thistle, medicinal plants containing ether oils (peppermint and *Helichrysi flos*) and bitter substances (yarrow, dandelion, buckbean). St. Mary thistle (*Cardui mariaum*) is a medicinal plant, known for its anti-hepatitis effects in phytotherapy. When ether oil of peppermint (*Mentha piperita* L.) and *Helichrysum arenarium* are added to St. Mary thistle, as well as bitter substances of yarrow (*Achillea millefollium*), buckbean (*Menyanthes trifoliata*), and especially dandelion (*Taraxaci radix*) which improves gall flow, the inflamation and congestion of the liver get weakened, metabolic processes and gall secretion get improved, and St. Mary thistle restores liver cells. Active matters responsible for the positive influence:

1. *Cardui marianum*

Active substance of St. Mary thistle—sylimarin—it is a mixture of various flavonolignans (sylibin, sylicristin and sylidionin).

1. It protects liver against toxins by blocking joint spots of liver cell outer membrane, thus making it difficult for toxins to enter 2. It stimulates protein synthesis in liver, thus accelerating the regeneration of a previously damaged liver.

2. *Millefolii flos* ether oils, with azulen as prevailing one

3. *Taraxaci radix* bitter substances, saponins, especially inulin

4. *Menthae pipperiate folium* ether oils: menthol 60%

5. *Helichrysi flos* ether oils, flavonoids, bitter substances

6. *Menyanthes trifoliata herba* bitter substances, glycosides, flavonoids

In its preparation, the composition is consisted of:

1. Tea mixture and/or, 2. alcoholic herbal extract 3. capsule containing:

| Tea | | |
|---|---|---|
| *Millefollii flos* - yarrow | 5–15 w/w %, preferably 10 w/w % |
| *Taraxaci radix* - dandelion | 5–15 w/w %, preferably 10 w/w % |
| *Menthae piperitae folium* - peppermint | 24–44 w/w %, preferably 34 w/w % |
| *Cardui mariae* - St. Mary thistle | 30–50 w/w %, preferably 40 w/w % |

| | -continued | |
|---|---|---|
| Helichrysi flos | 2–4 w/w %, preferably 3 w/w % | |
| Menyanthes trifoliata - buckbean | 2–4 w/w %, preferably 3 w/w % | |

According to what has been said so far, preferable shares of herbal substances for 60 g of tea would be:

| Tea - 60 g: | Millefollii flos - yarrow | 6 g (10 w/w %) |
|---|---|---|
| | Taraxaci radix - dandelion | 6 g (10 w/w %) |
| | Menthae piperiate folium - peppermint | 20 g (34 w/w %) |
| | Cardui mariae folium - St. Mary thistle | 24 g (40 w/w %) |
| | Heliechrysi flos | 2 g (3 w/w %) |
| | Menyanthes trifoliata - buckbean | 2 g (3 w/w %) |
| | | 60 g (100%) |

According to the invention, alcoholic extract was obtained from:

| Cardui mariae fructus | 90–100 w/w % |
|---|---|
| Helichrysi flos | 0–10 w/w % |

Whereby alcohol used for the extraction is 70% ethanol. In the most preferable preparation, the alcoholic herbal extract contains alcoholic herbal extract—50 ml:

| Cardui mariae fructus | 15 w/w % |
|---|---|
| Helichrysi flos | 5 w/w % |
| Extract in ethanol (70% pure) | 80 w/w % |
| | 100% |

I) Hepatovit—Drops 50 ml

Sylimarin is soluble in ethanol drops, so the drops of extract have higher phytotherapeutic value than St. Mary thistle-based remedies known so far. Duration of the extraction is 10 days, at room temperature, preferably between 4 and 12 C., in dark rooms unexposed to the sun, and in plastic dishes. It has been proved that solubility of the chemical compound sylimarin is the highest in ethanol. Human re-absorbs these drops very quickly, unlike remedies on the basis of St. Mary thistle seeds that have been made so far.

Higher solubility in water and organism has been proved.

St. Mary thistle seeds are to be put in ethanol (70% pure), and occasionally stirred during the extraction.

A few days after the drops are adminstered, the liver starts taking over its function, which has already been occasionally failing or has not been working properly.

Helichrysi flos is added because of its soothing effect on metabolism and the secretion of gall.

II) Hepatovit—Tea Mixture 60 g

Shows very good synergic effect of all six components on a damaged liver, even when the accumulation of water in the liver has already began, and the liver has started to swell. The water disappears and the liver recovers gradually by the performance of the composition according to the invention.

However, the efficacy has also been proved because sylimarin from St. Mary thistle leaf in our composition has synergic effect. This means that its effects are better and more efficient when combined with other components than when acting alone.

The composition is applied against chronic inflammatory liver diseases, alcohol-based damages, drug-based and chemical-based damages, radiation consequences, and as an additional therapy against acute and chronic hepatitis.

The tea and the extract function on the same principle. The basic active substance in the tea mixture, as well as in the extract, is sylimarin. The difference is that sylimarin in the extract is present in bigger amount. On the other side, there are also other herbal components in the tea, the components that synergiclly assist the performance of the basic active substance, thus providing the effect which is more overall. Therefore, regarding the therapy, the most preferable performance of the invetion includes the application of the tea and the extract simultaneously because the highest efficacy of the preparation was noticed in such case.

Although in cases of light forms of liver diseases, only the tea or the extract used individually can cure.

The composition significantly improves activity of the liver in a range of chronic and acute diseases, from hepatitis to cirrhosis. The composition was administered to volunteers suffering from such diseases, and they explained their state afterwards. Here are several examples:

1. In practice, the composition has proved itself as extremely efficient in cases of swelled (i.e. fatty liver). A few days after the administration of the tea and the drops, the food digestion got improved and its use got correct, meaning that the liver started functioning correctly again.
2. Water in liver, in large volumes
    Percentage share of water was reduced, whereby the distention was reduced as well. The patient began consuming food normally again.
3. Alcohol-based damages
    The normalisation of liver functioning occurred by regular administration of "Hepatovit" and by quitting alcohol
4. Hepatitis
    Damaged liver started functioning properly after the preparation had been administered for a few weeks.
5. Remedies
    (Referring to some remedies which cause the cessation of vitamin K production). Liver starts synthesizing vitamin K, which is a key substance for the coagulation of blood, by the administration of our compositions.

The compositions described so far in this application have soothing effect on liver, helping its protection and regeneration. They are the tea and the drops. All six components from the tea mixture have a very good synergic effect. Sylimarin is soluble in ethanol drops which have better phytotherapeutical value in comparsion with tea mixture. This is due to added Helichrysi flos, causing the drops to function soothingly on the metabolism of liver and the secretion of gall.

Therefore, the prepared compositions on the basis of sylimarin, and in the form of capsules (4% Sylimarin) and forte capsules (70–80% Sylimarin), have stronger pharmacological effect in comparison with the tea and the drops. This is due to higher presence of active substance of Sylimarin, causing the composition to be more efficient in case of more serious liver diseases. Although the presence of sylimarin was proved in St. Mary thistle leaves, little has been done regarding the quantitative and qualitative determination of the substance. The use of St. Mary thistle leaves was given up because the concentration of sylimarin in St. Mary thistle fruit is higher, and sylimarin itself could easily be determined by the method of thin-layer chromatography according to pharmacopeia. Therefore, the "problem" with sylimarin from St. Mary thistle leaf is that it is linked into compounds, as having been proved by the analyses of our herbal composition.

DESCRIPTION OF CAPSULE INVENTION IN DETAIL

According to the invention, the composition is consisted of:

| | |
|---|---|
| *Menthae piperitae folium* - peppermint leaf 20% w/w % | 15–20 w/w, preferably |
| *Taraxaci radix* - dandelion root 15 w/w % | 10–20 w/w %, preferably |
| *Sitybi mariae fructus* - St. Mary thistle fruit 63 w/w % | 53–73 w/w %, preferably |
| Mg-stearate 2% w/w % | 1–3 w/w %, preferably |
| Total | 100% |

According to what has been said so far, the preferable amounts of herbal components in a 200 mg capsule would be:

| | |
|---|---|
| *Menthae piperitae folium* - peppermint leaf | 40 mg (20 w/w %) |
| *Taraxaci radix* - dandelion root | 30 mg (15 w/w %) |
| *Silybi mariae fructus* - St Mary thistle fruit | 127 mg (63 w/w %) |
| Mg-stearate | 3 mg (2 w/w %) |
| | 200 mg (100%) |

Forte Capsules

According to the invention, the composition is consisted of:

| | |
|---|---|
| *Menthae piperitae folium* - peppermint leaf 20 w/w % | 15–25 w/w %, preferably |
| *Taraxaci radix* - dandelion root 15 w/w % | 10–20 w/w %, preferably |
| Isolated sylimarin 63 w/w % | 53–73 w/w %, preferably |
| Mg-stearate 2 w/w % | 1–3 w/w %, preferably |
| Total | 100% |

According to what has been said so far, the preferable amounts of herbal components in a 200 mg capsule would be:

| | |
|---|---|
| *Menthae piperitae folium* - peppermint leaf | 40 mg (20 w/w %) |
| *Taraxaci radix* - dandelion root | 30 mg (15 w/w %) |
| Isolated sylimarin | 127 mg (63 w/w %) |
| Mg-stearate | 3 mg (2 w/w %) |
| | 200 mg (100%) |

I) Capsules—200 mg, a Dietetic Product Containing 4% Natural Sylimarin

| | |
|---|---|
| *Menthae piperitae folium* - peppermint leaf | 40 mg |
| *Taraxaci radix* - dandelion root | 30 mg |
| *Silybi mariae fructus* - St. Mary thistle fruit (4%) | 127 mg |
| Mg-stearate | 3 mg |

II) Forte Capsules—200 mg, a Dietetic Product Containing 70–80% Natural Sylimarin

| | |
|---|---|
| *Menthae piperitae folium* - peppermint leaf | 40 mg |
| *Taraxaci radix* - dandelion root | 30 mg |
| Isolated sylimarin (70–80%) | 127 mg |
| Mg-stearate | 3 mg |

Preparation:

Ripe and dried St. Mary thistle fruits are grinded, the skin is removed by the blowing method, and the remains are grinded once again. Sylimarin is then being singled out by one of the patented methods. These methods are:

a) The method of Sylimarin extraction by using ethyl-acetate gives 70–80% Sylimarin (U.S. Pat. No. 4,368,195, 11 Jan. 1983.)

b) The method of Sylimarin isolation, giving 100% Sylimarin (U.S. Pat. No. 6,309,678, 30 Oct. 2001.)

However, the efficacy has also been proved because Sylimarin from St. Mary thistle leaf in our preparation has synergic effect (i.e. it acts better and more efficiently when combined with other components than when acting alone).

The compound is used in case of chronic liver diseases, alcohol-based damages, remedy-based and chemical-based damages, radiation consequences, and as an additional therapy in case of acute and chronic hepatitis. The basic active substance in the capsules is sylimarin, with its presence higher in Hepatovit forte capsules, but both capsules act on the same principle. On the other hand, the rest of herbal components are also in the capsules, synergicly assisting the performance of the basic active substance, thus ensuring more overall effect.

This dietetic composition significantly improves the activity of liver, doing so in cases ranging from acute hepatitis diseases to liver cirrhosis. Volunteers suffering from this kind of diseases used the composition and explained their condition. Here are some examples:

1. In practice, the composition was proved to be extremely efficient in case of swelled (i.e. fatty liver). After a few days of capsule administration, the food digestion got improved and the use of food proper, meaning that the liver resumed functioning properly.

2. Water in liver, in large volumes
   The percentage share of water was reduced, whereby the distention was reduced as well. The patient began consuming food normally again.
3. Alcohol-based damages
   The normalisation of liver functioning occurred by regular administration of "Hepatovit" and by quitting alcohol.
4. Hepatitis
   Damaged liver started functioning properly after the preparation had been administered for a few weeks. Hepatovit contains anti-oxidans that inhibit the acitvity of free radicals, and increase the amount of glutation in liver which has positive effect in case of hepatitis.
5. Remedies
   (Referring to some remedies which cause the cessation of vitamin K production). Liver starts synthesizing vitamin K, which is a key substance for the coagulation of blood, by the administration of our compositions. The composition has anthipalni effect on blood and the increase of T-lymphocytes
6. Stonegalls
   The composition has inhibiting effect on the crystallisation of gall and prevents the formation of stonegalls. It improves the intestinal peristaltics, and the solubility of fatty substances in gall.
7. Protective factor in case of cancer formation
   Sylimarin—active substance in the composition has inhibiting effect on enzyme-ornitin-decarboxylase (ODC) which induces the formation of skin cancer.
8. Haematological anemia
   The disease has been known as the lack of enzyme glucose-6-phosphate dehydrogenase. The lack of it causes the destruction of red blood cells.
   The composition has positive effect in case of haematological anemia, protecting the membranes of red blood cells from hemolisis and lipid peroxidation.
9. Production of female sex hormons
   It has a positive effect on the regulation of production of female sex hormons (estrogen), and helps during periods and headaches related to the menstrual cycle.
10. It acts as a depurative (purifying blood and liver), and as a diuretic (disposing of toxins through urine).

No side effects have been noticed so far, and pre-clinical researches are under way.

Active substance of St. Mary thistle (*Sylibum marianum*)—SYLIMARIN

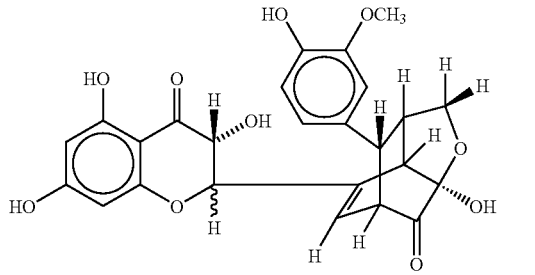

Sitibinin

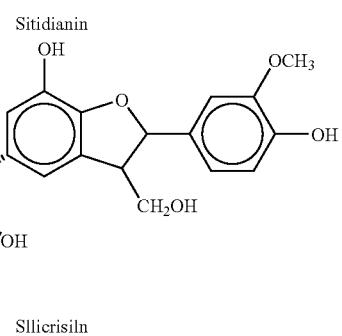

Sitidianin

Sllicrisiln

No side effects have been noticed so far, and pre-clinical researches are under way.

The invention claimed is:

1. A composition of herbal origin, comprising:
   a) Sylimarin,
   b) *Millefolii flos* yarrow flower,
   c) *Taraxaci radix* dandelion root,
   d) *Menthae piperitae* folium peppermint leaf,
   e) *Helichysi flos*, and
   f) *Menyanthes trifoliate* folium buckbean leaf wherein the sylmarin is isolated or present in an extract of St. Mary thistle plant.

2. The composition of claim 1, where the components are present in the following amounts:

| | |
|---|---|
| *Millefolii fibs* - yarrow flower, | 5–15 w/w % |
| *Taraxaci radix* - dandelion root, | 5–15 w/w % |
| *Menthae piperitae folim* - peppermint leaf, | 24–44 w/w % |
| *Cardui mariae folium* - St. Mary thistle leaf, | 30–50 w/w % |
| *Helichrysi flos*, and | 2–4 w/w % |
| *Menvanthes trifoliate folim*- buckbean leaf | 2–4 w/w %. |

3. The composition of claim 1, where the components are present in the following amounts:

| | |
|---|---|
| *Millefolii fibs* - yarrow flower, | 10 w/w % |
| *Taraxaci radix* - dandelion root, | 10 w/w % |
| *Menthae piperitae folium* - peppermint leaf, | 34 w/w % |
| *Cardui mariae folium* - St. Mary thistle leaf, | 40 w/w % |
| *Helichrysi flos*, and | 3 w/w % |
| *Menvanthes trifoliate folium* - buckbean leaf | 3 w/w %. |

* * * * *

UNITED STATES PATENT AND TRADEMARK OFFICE
CERTIFICATE OF CORRECTION

| | | |
|---|---|---|
| PATENT NO. | : 7,172,774 B2 | |
| APPLICATION NO. | : 10/880749 | |
| DATED | : February 6, 2007 | |
| INVENTOR(S) | : Vladimir Leko | |

It is certified that error appears in the above-identified patent and that said Letters Patent is hereby corrected as shown below:

On the Title Page, Item (63) should read,

Related U.S. Application Data

Continuation of application No. PCT/HR02/00038, filed August 30, 2002.

On the Title Page Item (30) should read,

Foreign Application Priority Data

CROATIA P20010789A filed October 25, 2001

CROATIA P20020361A filed April 25, 2002

Signed and Sealed this

Twenty-second Day of May, 2007

JON W. DUDAS
*Director of the United States Patent and Trademark Office*